United States Patent
de Villiers et al.

(10) Patent No.: US 11,857,438 B2
(45) Date of Patent: Jan. 2, 2024

(54) METHODS AND APPARATUS FOR INTERVERTEBRAL DISC PROSTHESIS INSERTION

(71) Applicant: Simplify Medical Pty Ltd, Sunnyvale, CA (US)

(72) Inventors: Malan de Villiers, Wapadrand (ZA); Ulrich Hahnle, Johannesburg (ZA); David Hovda, Mountain View, CA (US)

(73) Assignee: Simplify Medical Pty Ltd, Sunnyvale, CA (US)

(*) Notice: Subject to any disclaimer, the term of this patent is extended or adjusted under 35 U.S.C. 154(b) by 351 days.

(21) Appl. No.: 17/111,357

(22) Filed: Dec. 3, 2020

(65) Prior Publication Data
US 2021/0106437 A1   Apr. 15, 2021

Related U.S. Application Data

(60) Continuation of application No. 16/122,805, filed on Sep. 5, 2018, now Pat. No. 10,888,437, which is a
(Continued)

(51) Int. Cl.
*A61F 2/46* (2006.01)
*A61F 2/44* (2006.01)
(Continued)

(52) U.S. Cl.
CPC ............ *A61F 2/4611* (2013.01); *A61F 2/442* (2013.01); *A61F 2/4425* (2013.01);
(Continued)

(58) Field of Classification Search
CPC ........... A61B 17/025; A61B 2017/0256; A61F 2/4611; A61F 2/442; A61F 2/4425; A61F 2/4455; A61F 2/4465
(Continued)

(56) References Cited

U.S. PATENT DOCUMENTS

| | | | |
|---|---|---|---|
| 3,486,505 A | 12/1969 | Gordon | |
| 3,867,728 A | 2/1975 | Stubstad et al. | |

(Continued)

FOREIGN PATENT DOCUMENTS

| | | | |
|---|---|---|---|
| DE | 3023353 A1 | 4/1981 | |
| DE | 10035182 A1 | 2/2002 | |

(Continued)

OTHER PUBLICATIONS

Buttner-Janz, The Development of the Artificial Disc. Introduction, pp. 1-18, Library of Congress Catalogue No. 92-75582, ISBN 0-9635430-0-8 (1989).
(Continued)

*Primary Examiner* — Matthew J Lawson

(57) ABSTRACT

A method for inserting an intervertebral disc prosthesis into a space between two vertebrae involves inserting the prosthesis partway into the space under constraint to prevent endplates of the prosthesis from articulating, releasing the prosthesis from constraint, and inserting the unconstrained prosthesis farther into the space. In some embodiments, the method involves grasping the prosthesis with a grasping device to insert the prosthesis partway under constraint, loosing the grasping device to release the prosthesis from constraint, and pushing the prosthesis farther into the disc space using the grasping device and/or one or more separate pusher devices. A system includes a grasping device, at least one separate pushing device, and optionally a vertebral spreading device and/or a vertebral midline indicator device.

20 Claims, 7 Drawing Sheets

Related U.S. Application Data continuation of application No. 14/612,550, filed on Feb. 3, 2015, now Pat. No. 10,085,853, which is a continuation of application No. 12/650,231, filed on Dec. 30, 2009, now Pat. No. 8,974,531, which is a continuation of application No. 12/044,175, filed on Mar. 7, 2008, now abandoned, which is a division of application No. 10/913,780, filed on Aug. 6, 2004, now Pat. No. 7,585,326.

(51) Int. Cl.
*A61B 17/02* (2006.01)
*A61F 2/30* (2006.01)

(52) U.S. Cl.
CPC .......... *A61F 2/4455* (2013.01); *A61F 2/4465* (2013.01); *A61B 17/025* (2013.01); *A61B 2017/0256* (2013.01); *A61F 2/4603* (2013.01); *A61F 2002/30518* (2013.01); *A61F 2002/30649* (2013.01); *A61F 2002/443* (2013.01); *A61F 2002/4615* (2013.01); *A61F 2002/4622* (2013.01); *A61F 2002/4627* (2013.01); *A61F 2002/4628* (2013.01)

(58) Field of Classification Search
USPC .......................................... 623/17.11–17.16
See application file for complete search history.

(56) References Cited

U.S. PATENT DOCUMENTS

| | | |
|---|---|---|
| 4,309,777 A | 1/1982 | Patil |
| 4,531,917 A | 7/1985 | Linkow, I et al. |
| 4,566,466 A | 1/1986 | Ripple et al. |
| 4,619,660 A | 10/1986 | Christiansen et al. |
| 4,673,407 A | 6/1987 | Martin |
| 4,759,766 A | 7/1988 | Buettner-Janz Karin et al. |
| 4,759,769 A | 7/1988 | Hedman et al. |
| 4,834,757 A | 5/1989 | Brantigan |
| 4,863,477 A | 9/1989 | Monson |
| 4,904,261 A | 2/1990 | Dove et al. |
| 4,917,704 A | 4/1990 | Frey et al. |
| 4,932,969 A | 6/1990 | Frey et al. |
| 4,946,378 A | 8/1990 | Hirayama et al. |
| 4,997,432 A | 3/1991 | Keller et al. |
| 5,035,716 A | 7/1991 | Downey |
| 5,057,108 A | 10/1991 | Shetty et al. |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |
| 5,282,661 A | 2/1994 | Arnberger |
| 5,282,861 A | 2/1994 | Kaplan |
| 5,306,308 A | 4/1994 | Gross et al. |
| 5,314,477 A | 5/1994 | Marnay |
| 5,320,644 A | 6/1994 | Baumgartner |
| 5,370,697 A | 12/1994 | Baumgartner et al. |
| 5,394,457 A | 2/1995 | Leibinger et al. |
| 5,401,269 A | 3/1995 | Buettner-Janz Karin et al. |
| 5,415,704 A | 5/1995 | Davidson |
| 5,458,642 A | 10/1995 | Beer et al. |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Büttner-Janz |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,709,683 A | 1/1998 | Bagby |
| 5,728,159 A | 3/1998 | Stroever et al. |
| 5,741,253 A | 4/1998 | Michelson |
| 5,776,198 A | 7/1998 | Rabbe et al. |
| 5,782,832 A | 7/1998 | Larsen et al. |
| 5,797,909 A | 8/1998 | Michelson |
| 5,824,094 A | 10/1998 | Serhan et al. |
| 5,836,948 A | 11/1998 | Zucherman et al. |
| 5,865,846 A | 2/1999 | Bryan et al. |
| 5,865,848 A | 2/1999 | Baker |
| 5,888,226 A | 3/1999 | Rogozinski |
| 5,895,428 A | 4/1999 | Berry |
| 5,899,901 A | 5/1999 | Middleton |
| 5,899,911 A | 5/1999 | Carter |
| 5,928,284 A | 7/1999 | Mehdizadeh |
| 5,989,251 A | 11/1999 | Nichols |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,761 A | 3/2000 | Li et al. |
| 6,039,763 A | 3/2000 | Shelokov |
| 6,080,155 A | 6/2000 | Michelson |
| 6,083,228 A | 7/2000 | Michelson |
| 6,086,613 A | 7/2000 | Camino et al. |
| 6,096,038 A | 8/2000 | Michelson |
| 6,132,465 A | 10/2000 | Ray et al. |
| 6,136,031 A | 10/2000 | Middleton |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,174,311 B1 | 1/2001 | Branch et al. |
| 6,176,881 B1 | 1/2001 | Schaer et al. |
| 6,193,757 B1 | 2/2001 | Foley et al. |
| 6,224,595 B1 | 5/2001 | Michelson |
| 6,224,607 B1 | 5/2001 | Michelson |
| 6,231,609 B1 | 5/2001 | Mehdizadeh |
| 6,235,030 B1 | 5/2001 | Zucherman et al. |
| 6,261,296 B1 | 7/2001 | Aebi et al. |
| 6,264,695 B1 | 7/2001 | Stoy |
| 6,290,726 B1 | 9/2001 | Pope et al. |
| 6,296,664 B1 | 10/2001 | Middleton |
| 6,315,797 B1 | 11/2001 | Middleton |
| 6,319,257 B1 | 11/2001 | Carignan et al. |
| 6,322,567 B1 | 11/2001 | Mittelstadt et al. |
| 6,336,941 B1 | 1/2002 | Subba et al. |
| 6,348,071 B1 | 2/2002 | Steffee et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,395,032 B1 | 5/2002 | Gauchet |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,436,098 B1 | 8/2002 | Michelson |
| 6,440,139 B2 | 8/2002 | Michelson |
| 6,440,142 B1* | 8/2002 | Ralph .................. A61F 2/4611 606/86 R |
| 6,447,544 B1 | 9/2002 | Michelson |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |
| 6,554,864 B2 | 4/2003 | Ralph et al. |
| 6,562,047 B2 | 5/2003 | Ralph et al. |
| 6,562,074 B2 | 5/2003 | Gerbec et al. |
| 6,565,574 B2 | 5/2003 | Michelson |
| 6,582,466 B1 | 6/2003 | Gauchet |
| 6,582,468 B1 | 6/2003 | Gauchet |

(56) References Cited

U.S. PATENT DOCUMENTS

| | | |
|---|---|---|
| 6,592,624 B1 | 7/2003 | Fraser et al. |
| 6,599,294 B2 | 7/2003 | Fuss et al. |
| 6,607,558 B2 | 8/2003 | Kuras |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,648,895 B2 | 11/2003 | Burkus et al. |
| 6,652,533 B2 | 11/2003 | O'Neil |
| 6,660,038 B2 | 12/2003 | Boyer et al. |
| 6,666,866 B2 | 12/2003 | Martz et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,819 B2 | 3/2004 | Zucherman et al. |
| 6,712,825 B2 | 3/2004 | Aebi et al. |
| 6,719,794 B2 | 4/2004 | Gerber et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,733,532 B1 | 5/2004 | Gauchet et al. |
| 6,740,118 B2 | 5/2004 | Eisermann et al. |
| 6,740,119 B2 | 5/2004 | Ralph et al. |
| 6,752,832 B2 | 6/2004 | Neumann |
| 6,755,841 B2 | 6/2004 | Fraser et al. |
| 6,764,512 B2 | 7/2004 | Keller |
| 6,764,515 B2 | 7/2004 | Ralph et al. |
| 6,770,095 B2 | 8/2004 | Grinberg et al. |
| 6,790,233 B2 | 9/2004 | Brodke et al. |
| 6,793,678 B2 | 9/2004 | Hawkins |
| 6,814,737 B2 | 11/2004 | Cauthen |
| 6,821,298 B1 | 11/2004 | Jackson |
| 6,827,740 B1 | 12/2004 | Michelson |
| 6,830,570 B1 | 12/2004 | Frey et al. |
| 6,846,328 B2 | 1/2005 | Cauthen |
| 6,852,126 B2 | 2/2005 | Ahlgren |
| 6,863,673 B2 | 3/2005 | Gerbec et al. |
| 6,875,213 B2 | 4/2005 | Michelson |
| 6,896,680 B2 | 5/2005 | Michelson |
| 6,899,735 B2 | 5/2005 | Coates et al. |
| 6,936,071 B1 | 8/2005 | Marnay et al. |
| 6,936,132 B2 | 8/2005 | Topolnitsky |
| 6,964,686 B2 | 11/2005 | Gordon |
| 6,966,929 B2 | 11/2005 | Mitchell |
| 6,966,931 B2 | 11/2005 | Huang |
| 6,981,989 B1 | 1/2006 | Fleischmann et al. |
| 6,986,788 B2 | 1/2006 | Paul et al. |
| 6,989,011 B2 | 1/2006 | Paul et al. |
| 6,994,727 B2 | 2/2006 | Khandkar et al. |
| 7,011,684 B2 | 3/2006 | Eckman |
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |
| 7,083,651 B2 | 8/2006 | Diaz et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,169,182 B2 | 1/2007 | Errico et al. |
| 7,179,294 B2 | 2/2007 | Eisermann et al. |
| 7,182,784 B2 | 2/2007 | Evans et al. |
| 7,198,644 B2 | 4/2007 | Schultz et al. |
| 7,204,852 B2 * | 4/2007 | Marnay ............... A61F 2/4611 606/53 |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,082 B2 | 6/2007 | Bartish et al. |
| 7,235,085 B1 | 6/2007 | Tahir |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,270,682 B2 | 9/2007 | Frigg et al. |
| 7,303,582 B2 | 12/2007 | Brady |
| 7,303,583 B1 | 12/2007 | Schaer et al. |
| 7,318,839 B2 | 1/2008 | Malberg, I et al. |
| 7,326,250 B2 | 2/2008 | Beaurain et al. |
| 7,331,995 B2 | 2/2008 | Eisermann et al. |
| 7,429,270 B2 | 9/2008 | Baumgartner et al. |
| 7,442,211 B2 | 10/2008 | De et al. |
| 7,452,380 B2 | 11/2008 | Zubok et al. |
| 7,491,241 B2 | 2/2009 | Errico et al. |
| 7,494,508 B2 | 2/2009 | Zeegers et al. |
| 7,517,363 B2 | 4/2009 | Rogers et al. |
| 7,531,001 B2 | 5/2009 | De et al. |
| 7,549,995 B2 | 6/2009 | Schultz |
| 7,563,284 B2 | 7/2009 | Coppes et al. |
| 7,563,286 B2 | 7/2009 | Gerber et al. |
| 7,585,326 B2 | 9/2009 | De et al. |
| 7,637,913 B2 | 12/2009 | De et al. |
| 7,708,776 B1 | 5/2010 | Blain et al. |
| 7,708,777 B2 | 5/2010 | O'Neil et al. |
| 7,731,753 B2 | 6/2010 | Reo et al. |
| 7,753,956 B2 | 7/2010 | De et al. |
| 7,803,162 B2 * | 9/2010 | Marnay ............... A61F 2/4425 623/17.16 |
| 8,206,447 B2 | 6/2012 | De et al. |
| 8,348,958 B2 | 1/2013 | Ralph et al. |
| 8,388,684 B2 | 3/2013 | Bao et al. |
| 8,388,864 B2 | 3/2013 | Bormann et al. |
| 8,974,531 B2 | 3/2015 | De et al. |
| 9,839,532 B2 | 12/2017 | De et al. |
| 9,956,091 B2 | 5/2018 | De et al. |
| 10,085,853 B2 | 10/2018 | Villiers et al. |
| 2001/0016773 A1 | 8/2001 | Serhan et al. |
| 2001/0029377 A1 | 10/2001 | Aebi et al. |
| 2001/0031969 A1 | 10/2001 | Aebi et al. |
| 2002/0016550 A1 | 2/2002 | Sweeney et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0014114 A1 | 1/2003 | Ralph et al. |
| 2003/0016773 A1 | 1/2003 | Atungsiri et al. |
| 2003/0023245 A1 | 1/2003 | Ralph et al. |
| 2003/0028249 A1 | 2/2003 | Baccelli et al. |
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0069586 A1 | 4/2003 | Errico et al. |
| 2003/0074070 A1 | 4/2003 | Errico et al. |
| 2003/0074076 A1 | 4/2003 | Ferree et al. |
| 2003/0078590 A1 | 4/2003 | Errico et al. |
| 2003/0083747 A1 | 5/2003 | Winterbottom et al. |
| 2003/0100951 A1 | 5/2003 | Serhan et al. |
| 2003/0125739 A1 | 7/2003 | Bagga et al. |
| 2003/0130662 A1 | 7/2003 | Michelson |
| 2003/0135220 A1 | 7/2003 | Cauthen |
| 2003/0135277 A1 | 7/2003 | Bryan et al. |
| 2003/0139812 A1 | 7/2003 | Garcia et al. |
| 2003/0153916 A1 | 8/2003 | Michelson |
| 2003/0187448 A1 | 10/2003 | Michelson |
| 2003/0191536 A1 | 10/2003 | Ferree |

(56) References Cited

U.S. PATENT DOCUMENTS

| | | |
|---|---|---|
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0216737 A1 | 11/2003 | Biscup |
| 2003/0229358 A1 | 12/2003 | Errico et al. |
| 2003/0233145 A1 | 12/2003 | Landry et al. |
| 2003/0233155 A1 | 12/2003 | Slemmer et al. |
| 2004/0002761 A1 | 1/2004 | Rogers et al. |
| 2004/0024407 A1 | 2/2004 | Ralph et al. |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073311 A1 | 4/2004 | Ferree |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0117021 A1 | 6/2004 | Biedermann et al. |
| 2004/0143270 A1 | 7/2004 | Zucherman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 | 10/2004 | Suddaby |
| 2004/0225295 A1 | 11/2004 | Zubok et al. |
| 2004/0225365 A1 | 11/2004 | Eisermann et al. |
| 2004/0236426 A1 | 11/2004 | Ralph et al. |
| 2004/0243238 A1 | 12/2004 | Arnin et al. |
| 2004/0254644 A1 | 12/2004 | Taylor |
| 2005/0015094 A1 | 1/2005 | Keller |
| 2005/0015095 A1 | 1/2005 | Keller |
| 2005/0015152 A1 | 1/2005 | Sweeney |
| 2005/0021042 A1* | 1/2005 | Marnay ................ A61F 2/4611 606/99 |
| 2005/0021145 A1 | 1/2005 | De et al. |
| 2005/0021146 A1 | 1/2005 | De et al. |
| 2005/0027360 A1 | 2/2005 | Webb et al. |
| 2005/0033305 A1 | 2/2005 | Schultz |
| 2005/0038515 A1 | 2/2005 | Kunzler |
| 2005/0043800 A1 | 2/2005 | Paul et al. |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg et al. |
| 2005/0119747 A1 | 6/2005 | Fabris et al. |
| 2005/0143749 A1 | 6/2005 | Zalenski et al. |
| 2005/0143824 A1 | 6/2005 | Richelsoph et al. |
| 2005/0149189 A1 | 7/2005 | Mokhtar et al. |
| 2005/0154463 A1 | 7/2005 | Trieu |
| 2005/0165408 A1 | 7/2005 | Puno et al. |
| 2005/0171604 A1 | 8/2005 | Michalow |
| 2005/0192586 A1 | 9/2005 | Zucherman et al. |
| 2005/0192670 A1 | 9/2005 | Zubok et al. |
| 2005/0197706 A1 | 9/2005 | Hovorka et al. |
| 2005/0216081 A1 | 9/2005 | Taylor et al. |
| 2005/0216084 A1 | 9/2005 | Fleischmann et al. |
| 2005/0228500 A1 | 10/2005 | Kim et al. |
| 2005/0234553 A1 | 10/2005 | Gordon |
| 2005/0251260 A1 | 11/2005 | Gerber et al. |
| 2005/0251261 A1 | 11/2005 | Peterman |
| 2005/0251262 A1 | 11/2005 | De et al. |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish et al. |
| 2006/0015183 A1 | 1/2006 | Gilbert et al. |
| 2006/0020342 A1 | 1/2006 | Ferree et al. |
| 2006/0025862 A1 | 2/2006 | Villiers et al. |
| 2006/0029186 A1 | 2/2006 | De et al. |
| 2006/0030857 A1 | 2/2006 | De et al. |
| 2006/0030860 A1* | 2/2006 | Peterman ............... A61F 2/4611 606/99 |
| 2006/0030862 A1 | 2/2006 | De et al. |
| 2006/0036325 A1 | 2/2006 | Paul et al. |
| 2006/0041313 A1 | 2/2006 | Allard et al. |
| 2006/0041314 A1 | 2/2006 | Millard |
| 2006/0052870 A1 | 3/2006 | Ferree |
| 2006/0064169 A1 | 3/2006 | Ferree |
| 2006/0069439 A1 | 3/2006 | Zucherman et al. |
| 2006/0116768 A1 | 6/2006 | Krueger et al. |
| 2006/0142858 A1 | 6/2006 | Colleran et al. |
| 2006/0142862 A1 | 6/2006 | Diaz et al. |
| 2006/0155378 A1 | 7/2006 | Eckman |
| 2006/0167549 A1 | 7/2006 | Mathys, Jr. et al. |
| 2006/0178744 A1 | 8/2006 | De et al. |
| 2006/0178746 A1 | 8/2006 | Bartish, Jr. et al. |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz Karin et al. |
| 2006/0241641 A1 | 10/2006 | Albans et al. |
| 2006/0241766 A1 | 10/2006 | Felton et al. |
| 2006/0259144 A1 | 11/2006 | Trieu |
| 2006/0259146 A1 | 11/2006 | Navarro et al. |
| 2006/0265068 A1 | 11/2006 | Schwab |
| 2006/0265077 A1 | 11/2006 | Zwirkoski |
| 2006/0287728 A1 | 12/2006 | Mokhtar et al. |
| 2006/0293752 A1 | 12/2006 | Moumene et al. |
| 2006/0293753 A1 | 12/2006 | Thramann |
| 2006/0293754 A1 | 12/2006 | Devilliers et al. |
| 2007/0010826 A1 | 1/2007 | Rhoda et al. |
| 2007/0021837 A1 | 1/2007 | Ashman |
| 2007/0032875 A1 | 2/2007 | Blacklock et al. |
| 2007/0061011 A1 | 3/2007 | De et al. |
| 2007/0067035 A1 | 3/2007 | Falahee |
| 2007/0067036 A1 | 3/2007 | Hudgins et al. |
| 2007/0073398 A1 | 3/2007 | Fabian et al. |
| 2007/0093898 A1 | 4/2007 | Schwab et al. |
| 2007/0100453 A1 | 5/2007 | Parsons et al. |
| 2007/0100454 A1 | 5/2007 | Burgess et al. |
| 2007/0100456 A1 | 5/2007 | Dooris et al. |
| 2007/0123903 A1 | 5/2007 | Raymond et al. |
| 2007/0123904 A1 | 5/2007 | Stad et al. |
| 2007/0135923 A1 | 6/2007 | Peterman et al. |
| 2007/0162133 A1 | 7/2007 | Doubler et al. |
| 2007/0168033 A1 | 7/2007 | Kim et al. |
| 2007/0168036 A1 | 7/2007 | Ainsworth et al. |
| 2007/0179615 A1 | 8/2007 | Heinz et al. |
| 2007/0213821 A1 | 9/2007 | Kwak et al. |
| 2007/0233077 A1 | 10/2007 | Khalili |
| 2007/0233247 A1 | 10/2007 | Schwab |
| 2007/0233248 A1 | 10/2007 | Schwab et al. |
| 2007/0233251 A1 | 10/2007 | Abdou |
| 2007/0270970 A1 | 11/2007 | Trieu |
| 2007/0282449 A1 | 12/2007 | De et al. |
| 2007/0299521 A1 | 12/2007 | Glenn et al. |
| 2008/0015698 A1 | 1/2008 | Marino et al. |
| 2008/0015701 A1 | 1/2008 | Garcia et al. |
| 2008/0021557 A1 | 1/2008 | Trieu |
| 2008/0051900 A1 | 2/2008 | De et al. |
| 2008/0051901 A1 | 2/2008 | De et al. |
| 2008/0125864 A1 | 5/2008 | De et al. |
| 2008/0125865 A1 | 5/2008 | Abdelgany et al. |
| 2008/0133011 A1 | 6/2008 | De et al. |
| 2008/0154301 A1 | 6/2008 | De et al. |
| 2008/0154382 A1 | 6/2008 | De et al. |
| 2008/0215155 A1 | 9/2008 | De et al. |
| 2008/0221696 A1 | 9/2008 | De et al. |
| 2008/0228274 A1 | 9/2008 | De et al. |
| 2008/0228277 A1 | 9/2008 | De et al. |
| 2008/0294259 A1 | 11/2008 | De et al. |
| 2009/0043391 A1 | 2/2009 | De et al. |
| 2009/0048674 A1 | 2/2009 | Zubok et al. |
| 2009/0048677 A1 | 2/2009 | McLeod et al. |
| 2009/0076614 A1 | 3/2009 | Arramon |

(56) References Cited

U.S. PATENT DOCUMENTS

| | | |
|---|---|---|
| 2009/0105833 A1 | 4/2009 | Hovda et al. |
| 2009/0105834 A1 | 4/2009 | Hovda et al. |
| 2009/0105835 A1 | 4/2009 | Hovda et al. |
| 2009/0192617 A1 | 7/2009 | Arramon et al. |
| 2009/0205188 A1 | 8/2009 | De et al. |
| 2009/0210060 A1 | 8/2009 | De et al. |
| 2009/0222101 A1 | 9/2009 | De et al. |
| 2009/0276051 A1 | 11/2009 | Arramon et al. |
| 2009/0326542 A9* | 12/2009 | Errico .................... A61F 2/446 606/99 |
| 2009/0326656 A1 | 12/2009 | De et al. |
| 2010/0004746 A1 | 1/2010 | Arramon |
| 2010/0016972 A1 | 1/2010 | Jansen et al. |
| 2010/0016973 A1 | 1/2010 | De et al. |
| 2010/0030335 A1 | 2/2010 | Arramon |
| 2010/0049040 A1 | 2/2010 | De et al. |
| 2010/0069976 A1 | 3/2010 | De et al. |
| 2010/0076558 A1 | 3/2010 | De et al. |
| 2010/0087868 A1 | 4/2010 | Barr et al. |
| 2010/0100141 A1 | 4/2010 | De et al. |
| 2010/0179419 A1 | 7/2010 | De et al. |
| 2010/0331988 A1 | 12/2010 | Marnay et al. |
| 2013/0013073 A1 | 1/2013 | Villiers et al. |
| 2016/0220387 A1 | 8/2016 | De et al. |
| 2016/0250036 A1 | 9/2016 | De et al. |
| 2016/0250041 A1 | 9/2016 | De et al. |
| 2017/0100261 A1 | 4/2017 | Villiers et al. |
| 2017/0100262 A1 | 4/2017 | De et al. |
| 2017/0189205 A1 | 7/2017 | De et al. |

FOREIGN PATENT DOCUMENTS

| | | |
|---|---|---|
| DE | 20310433 U1 | 9/2003 |
| EP | 0333990 A2 | 9/1989 |
| EP | 0333990 A3 | 5/1990 |
| EP | 0560140 A1 | 9/1993 |
| EP | 0560141 A1 | 9/1993 |
| EP | 0591712 A1 | 4/1994 |
| EP | 0820740 A1 | 1/1998 |
| EP | 1142544 A1 | 10/2001 |
| EP | 1153582 A2 | 11/2001 |
| EP | 1153582 A3 | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1405615 A1 | 4/2004 |
| EP | 1417940 A1 | 5/2004 |
| EP | 1570813 A1 | 9/2005 |
| FR | 2803741 A1 | 7/2001 |
| JP | S61122859 A | 6/1986 |
| JP | S63164948 A | 7/1988 |
| JP | H01136655 A | 5/1989 |
| JP | H067391 A | 1/1994 |
| JP | 2002521090 A | 7/2002 |
| JP | 2003508119 A | 3/2003 |
| WO | WO-9113598 A1 | 9/1991 |
| WO | WO-9817209 A2 | 4/1998 |
| WO | WO-9817209 A3 | 9/1998 |
| WO | WO-9920209 A1 | 4/1999 |
| WO | WO-9930651 A1 | 6/1999 |
| WO | WO-0004851 A1 | 2/2000 |
| WO | WO-0035384 A1 | 6/2000 |
| WO | WO-0042954 A2 | 7/2000 |
| WO | WO-0042954 A3 | 11/2000 |
| WO | WO-0101893 A1 | 1/2001 |
| WO | WO-0115637 A1 | 3/2001 |
| WO | WO-0168003 A1 | 9/2001 |
| WO | WO-0211650 A2 | 2/2002 |
| WO | WO-02091909 A2 | 11/2002 |
| WO | WO-2004000170 A1 | 12/2003 |
| WO | WO-2004000171 A1 | 12/2003 |
| WO | WO-2004026187 A1 | 4/2004 |
| WO | WO-2004041131 A2 | 5/2004 |
| WO | WO-2004054477 A1 | 7/2004 |
| WO | WO-2004063061 A1 | 7/2004 |
| WO | WO-2005004756 A2 | 1/2005 |
| WO | WO-2005004757 A1 | 1/2005 |
| WO | WO-2005011523 A2 | 2/2005 |
| WO | WO-2005004756 A3 | 5/2005 |
| WO | WO-2005053580 A1 | 6/2005 |
| WO | WO-2005072662 A1 | 8/2005 |
| WO | WO-2005112834 A2 | 12/2005 |
| WO | WO-2005112834 A3 | 5/2006 |
| WO | WO-2006119092 A2 | 11/2006 |
| WO | WO-2006119092 A3 | 12/2006 |
| WO | WO-2007028098 A2 | 3/2007 |
| WO | WO-2007121320 A2 | 10/2007 |
| WO | WO-2007121320 A3 | 6/2008 |
| ZA | 200603171 | 9/2007 |

OTHER PUBLICATIONS

Co-pending U.S. Appl. No. 15/151,319, filed May 10, 2016.
Co-pending U.S. Appl. No. 15/151,332, filed May 10, 2016.
Co-pending U.S. Appl. No. 15/387,520, filed Dec. 21, 2016.
Co-pending U.S. Appl. No. 15/465,451, filed Mar. 21, 2017.
European search report and opinion dated May 2, 2012 for EP Application No. 05777414.3.
"Extended European search report and opinion dated Aug. 25, 2017 for EP Application No. 17172943.7".
Hellier, et al., Wear Studies for Development of an Intervertebral Disc Prosthesis. Spine, vol. 17 No. 6 Supplement pp. 86-96 (1992).
International search report and written opinion dated Apr. 6, 2007 for PCT/US2005/027049.
International search report dated Jul. 21, 2005 for PCT/US2005/026160.
International search report dated Jul. 27, 2007 for PCT/US2005/002263.
Japanese office action dated Feb. 12, 2010 for JP 2004-524870.
Lee, et al. Impact Response of the Intervertebral Disc in a Finite-Element Model. Spine. 2000; 25(19):2431-2439.
Lehuec, et al. Shock Absorption in Lumber Disc Prosthesis. Journal of Spinal Disorders & Techniques. 2003; 16(4):346-351.
Notice of allowance dated Apr. 27, 2012, for U.S. Appl. No. 12/044,165.
"Notice of Allowance dated Jun. 15, 2018 for U.S. Appl. No. 14/612,550".
Notice of allowance dated Jun. 29, 2009 for U.S. Appl. No. 10/913,780.
"Notice of Allowance dated Jul. 3, 2018 for U.S. Appl. No. 14/612,550".
"Notice of Allowance dated Oct. 25, 2017 for U.S. Appl. No. 15/387,495".
Notice of allowance dated Nov. 7, 2014 for U.S. Appl. No. 12/650,231.
Office action dated Jan. 14, 2014 for U.S. Appl. No. 12/650,231.
Office action dated Jan. 19, 2012 for U.S. Appl. No. 12/650,231.
Office action dated Feb. 5, 2009 for U.S. Appl. No. 10/913,780.
Office action dated Feb. 20, 2009 for U.S. Appl. No. 12/044,175.
Office action dated Mar. 22, 2011 for U.S. Appl. No. 12/044,165.
Office action dated Mar. 31, 2011 for U.S. Appl. No. 12/044,175.
"Office action dated Jun. 9, 2017 for U.S. Appl. No. 15/387,520".
"Office action dated Jun. 20, 2017 for U.S. Appl. No. 15/387,495".
Office action dated Jul. 3, 2013 for U.S. Appl. No. 12/650,231.
Office action dated Jul. 3, 2013 for U.S. Appl. No. 13/619,352.
Office action dated Jul. 6, 2011 for U.S. Appl. No. 12/650,231.
"Office action dated Jul. 6, 2017 for U.S. Appl. No. 15/465,451".
Office action dated Jul. 9, 2013 for U.S. Appl. No. 12/044,175.
Office action dated Jul. 16, 2007 for U.S. Appl. No. 10/913,780.
Office action dated Aug. 4, 2010 for U.S. Appl. No. 12/044,175.
"Office action dated Aug. 18, 2017 for U.S. Appl. No. 14/612,550".
"Office action dated Sep. 27, 2017 for U.S. Appl. No. 15/387,495".
Office action dated Oct. 5, 2011 for U.S. Appl. No. 12/044,165.
"Office action dated Oct. 25, 2017 for U.S. Appl. No. 15/465,451".
Office action dated Nov. 13, 2009 for U.S. Appl. No. 12/044,175.
"Office action dated Nov. 21, 2017 for U.S. Appl. No. 15/387,520".

(56) References Cited

OTHER PUBLICATIONS

Office action dated Dec. 23, 2010 for U.S. Appl. No. 12/650,231.
Office action dated Feb. 28, 2017 for U.S. Appl. No. 14/612,550.
U.S. Appl. No. 13/619,352, filed Sep. 14, 2012.
U.S. Appl. No. 14/612,550, filed Feb. 3, 2015.
"U.S. Appl. No. 14/612,550 Office Action dated Mar. 16, 2018".
"U.S. Appl. No. 15/465,451 Notice of Allowance dated Mar. 15, 2018".

* cited by examiner

METHODS AND APPARATUS FOR INTERVERTEBRAL DISC PROSTHESIS INSERTION

CROSS REFERENCE TO RELATED APPLICATION DATA

The present application is a continuation of U.S. patent application Ser. No. 16/122,805, filed Sep. 5, 2018, which is a continuation of U.S. patent application Ser. No. 14/612,550, filed Feb. 3, 2015, now U.S. Pat. No. 10,085,853, which is a continuation of U.S. patent application Ser. No. 12/650,231, filed Dec. 30, 2009, now U.S. Pat. No. 8,974,531, which is a continuation of U.S. patent application Ser. No. 12/044,175, filed Mar. 7, 2008, now abandoned, which is a divisional of U.S. patent application Ser. No. 10/913,780, filed Aug. 6, 2004, now U.S. Pat. No. 7,585,326; the full disclosures of which are incorporated herein by reference in their entirety.

BACKGROUND OF THE INVENTION

1. Field of the Invention

This invention relates to medical devices and methods. More specifically, the invention relates to intervertebral disc prostheses.

Back pain takes an enormous toll on the health and productivity of people around the world. According to the American Academy of Orthopedic Surgeons, approximately 80 percent of Americans will experience back pain at some time in their life. In just the year 2000, approximately 26 million visits were made to physicians' offices due to back problems in the United States. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral discs cause a patient pain and discomfort, surgery is often required. Traditionally, surgical procedures for treating intervertebral discs have involved discectomy (partial or total removal of a disc), with or without fusion of the two vertebrae adjacent to the disc. Fusion of the two vertebrae is achieved by inserting bone graft material between the two vertebrae such that the two vertebrae and the graft material grow together. Oftentimes, pins, rods, screws, cages and/or the like are inserted between the vertebrae to act as support structures to hold the vertebrae and graft material in place while they permanently fuse together. Although fusion often treats the back pain, it reduces the patient's ability to move, because the back cannot bend or twist at the fused area. In addition, fusion increases stresses at adjacent levels of the spine, potentially accelerating degeneration of these discs.

In an attempt to treat disc related pain without fusion, an alternative approach has been developed, in which a movable, implantable, artificial intervertebral disc (or "disc prosthesis") is inserted between two vertebrae. A number of different intervertebral disc prostheses are currently being developed. For example, the inventors of the present invention have developed disc prostheses described in U.S. patent application Ser. Nos. 10/855,817 and 10/855,253, previously incorporated by reference. Other examples of intervertebral disc prostheses are the LINK® SB CHARITE™ disc prosthesis (provided by DePuy Spine, Inc.) MOBIDISK™ disc prosthesis (provided by LDR Medical), the BRYAN™ cervical disc prosthesis (provided by Medtronic Sofamor Danek, Inc.), the PRODISC™ disc prosthesis or PRODISC-C™ disc prosthesis (from Synthes Stratec, Inc.), and the PCM™ disc prosthesis (provided by Cervitech, Inc.).

To insert an artificial intervertebral disc prosthesis, and indeed for performing most disc-related surgeries, it is typically necessary to gain access to the disc and the intervertebral space from an anterior to posterior direction (i.e., through the front of the patient), to avoid coming in contact with the spinal cord. Thus, surgical procedures on a disc are typically approached anteriorly through the neck or abdomen, depending on which disc (or discs) is being repaired. Methods for inserting a disc prosthesis generally involve removing the damaged disc, preparing the surfaces of the two vertebral bones to receive the prosthesis, spreading the two vertebrae apart using one or more spreading devices, and inserting the prosthesis into the space between the two vertebrae. Examples of such methods are described in U.S. Pat. Nos. 6,478,800, 6,235,030, 6,652,533, 6,689,132, 6,261,296 and 6,666,866, and in U.S. Patent Application Nos. 2001/0031969, 2001/0029377, 2003/0153916, 2002/0198532, 2004/0024407, 2003/0216737, 2003/0204261, 2003/0135220 and 2003/0014114. Due to the invasive nature of such procedures, one important goal is to reduce invasiveness, thus causing as little trauma to tissues surrounding the surgical site as possible.

The main drawback of currently available methods for inserting intervertebral disc prostheses is that they require a larger amount of spreading apart (or "distraction") of the two vertebrae than is optimal. Over-distraction is necessary when using such methods because it is important to insert the disc prosthesis all the way into the disc space, to position the center of rotation of the prosthesis closer to the posterior portion of the vertebrae than to the anterior portion. This allows the vertebrae to move as they were intended and avoids placing undue strain on the facet joints of the vertebrae or on other structures. To push a prosthesis toward the back of a disc space, however, it is typically necessary to spread the two vertebrae apart widely, since the anterior portion of the disc space is usually wider (or higher) than the posterior portion. In some methods, an artificial disc is placed by placing a first endplate into the space, placing a second endplate into the space, and then spreading the vertebrae wide enough to wedge a core in between the two endplates. In other methods, the vertebrae are spread apart as far as practicable, the whole prosthesis is inserted while one or more spreading devices are in place, and not until the prosthesis is completely inserted is the spreading device removed. In either case, as well as in other currently available methods, the two vertebrae adjacent the prosthesis are typically spread farther apart than would be desirable for a longer amount of time than would be desirable. In some cases, the posterior longitudinal ligament (PLL) is released, or "cut," to enable sufficient distraction for disc placement.

Distracting vertebrae can damage muscles, ligaments, nerves and/or other tissues in and around the vertebral column. Such damage may actually cause the patient to experience as much, or even more, pain after surgery than was caused by the original disc problem.

Therefore, as the use of intervertebral disc prostheses increases, an increasing need exists for improved methods and apparatus for inserting such prostheses. Ideally, such intervertebral prosthesis insertion methods and devices would provide for insertion of a prosthesis a desired distance into an intervertebral space while reducing the need for intervertebral distraction, thus preventing or at least reducing trauma to surrounding tissues. Also ideally, such insertion methods and devices would be relatively simple and easy to use, thereby reducing the overall invasiveness of the procedure. At least some of these objectives will be met by the present invention.

2. Description of the Background Art

A number of exemplary intervertebral disc prostheses are listed above. Published US patent applications 2002/0035400A1 and 2002/0128715A1 describe disc implants which comprise opposing plates with a core between them over which the plates can slide. The core receives one or more central posts, which are carried by the plates and which locate in opposite ends of a central opening in the core. Such arrangements limit the load bearing area available between the plates and core.

Other patents related to intervertebral disc prostheses include U.S. Pat. Nos. 4,759,766; 4,863,477; 4,997,432; 5,035,716; 5,071,437; 5,370,697; 5,401,269; 5,507,816; 5,534,030; 5,556,431; 5,674,296; 5,676,702; 5,702,450; 5,824,094; 5,865,846; 5,989,291; 6,001,130; 6,022,376; 6,039,763; 6,139,579; 6,156,067; 6,162,252; 6,315,797; 6,348,071; 6,368,350; 6,416,551; 6,592,624; 6,607,558 and 6,706,068. Other patent applications related to intervertebral disc prostheses include U.S. Patent Application Publication Nos.: 2003/0009224; 2003/0074076; 2003/0191536; 2003/0208271; 2003/0135277; 2003/0199982; 2001/0016773 and 2003/0100951. Other related patents include WO 01/01893A1, EP 1344507, EP 1344506, EP 1250898, EP 1306064, EP 1344508, EP 1344493, EP 1417940, EP 1142544, and EP 0333990.

BRIEF SUMMARY OF THE INVENTION

The present invention generally provides methods for inserting an intervertebral disc prosthesis, as well as devices and systems for performing the methods. One advantage of these improved methods is that a disc prosthesis may be inserted with minimal or reduced intervertebral distraction, thus avoiding trauma to tissues in and around the insertion site. Reduced distraction is generally achieved by inserting a prosthesis into an intervertebral space while allowing endplates of the prosthesis to articulate during at least part of the insertion process. For the purposes of this application, to "articulate" means to move relative to another structure. Thus, allowing endplates of an intervertebral prosthesis to articulate means that endplates are free to move relative to each other, relative to a core of the prosthesis, relative to a ball and socket joint of the prosthesis, relative to a mobile or fixed center of rotation of the prosthesis and/or the like. Although the following description often focuses on disc prostheses having two endplates and a core, various embodiments of the insertion method may be applied to any other intervertebral disc prosthesis. Articulation of the endplates during insertion allows the prosthesis to be pushed posteriorly into a disc space without excessive intervertebral distraction or significant forces being applied to the vertebrae, thus achieving desirable positioning of the prosthesis while avoiding trauma to surrounding muscles, ligaments, nerves and the like.

In one aspect of the present invention, a method of inserting an intervertebral prosthesis into a space between two adjacent vertebrae involves inserting the prosthesis partway into the space under constraint to prevent endplates of the prosthesis from articulating, releasing the prosthesis from constraint, and inserting the unconstrained prosthesis farther into the space. As mentioned above, in some embodiments, the endplates of the constrained prosthesis are prevented from articulating about a core of the prosthesis, while the endplates of the unconstrained prosthesis are generally free to articulate about the core to help the prosthesis conform to the space between the two vertebrae. In alternative embodiments, the unconstrained endplates may be free to articulate about a ball and socket joint or other structure.

In one embodiment, inserting the prosthesis partway under constraint involves grasping the endplates with an insertion tool such that they cannot move relative to the core and pushing the prosthesis partway into the space using the insertion tool. In such embodiments, releasing the prosthesis from constraint may involve loosening the insertion tool. In some embodiments, the loosened insertion tool may then be used to insert the unconstrained prosthesis farther into the intervertebral space. Additionally, or alternatively, a separate pusher tool may be used to insert the unconstrained prosthesis farther into the space.

In some embodiments, inserting the constrained prosthesis partway into the space between the vertebrae involves inserting the prosthesis less than halfway into the space. In one embodiment, for example, the constrained prosthesis is inserted about one third of the way into the space and then subsequently inserted farther into the space. In alternative embodiments, the constrained prosthesis may be pushed more than halfway into the space, less than one third of the way into the space, or any other suitable distance into the space. The unconstrained prosthesis is then inserted any desired distance farther into the intervertebral space. In some embodiments, for example, the prosthesis is inserted sufficiently far into the space that a center of rotation of the prosthesis is closer to the posterior edges of the vertebrae than to the anterior edges of the vertebrae.

In some embodiments, the prosthesis is inserted in approximately an anterior to posterior direction. In alternative embodiments, the prosthesis may be inserted in an anterolateral-to-posterior direction, lateral-to-lateral direction or posterior-to-anterior direction. Typically, inserting the unconstrained prosthesis farther into the space involves pushing the prosthesis into the space. In other embodiments, however, techniques other than pushing may be used to insert the prosthesis, such as pulling. In some embodiments, pushing the prosthesis farther into the space involves individually pushing upper and lower endplates of the prosthesis. Alternatively, or additionally, the upper and lower endplates of the prosthesis may be simultaneously pushed into the intervertebral space. In various embodiments, individual and simultaneous endplate pushing may be performed using the grasping device, a separate pusher device, or both.

In some embodiments, the method also includes inserting a vertebral spacing device at least partway into the space and manipulating the spacing device to increase a height of the space. An example of such a spacing device is described by the assignees of the present application in PCT Patent Application Number 2004/000171, filed Jan. 26, 2004, the full disclosure of which is hereby incorporated by reference. The spacing step is typically performed before inserting the constrained prosthesis partway into the intervertebral space. In some embodiments, inserting the constrained prosthesis partway into the intervertebral space comprises sliding the prosthesis between two opposing jaws of the spacing device. In such an embodiment, inserting the constrained prosthesis partway into the space may optionally further involve sliding at least one fin on at least one outer surface of the endplates through at least one corresponding slot in the opposing jaws. In one embodiment, such a fin (or fins) may then be slid into a corresponding slot formed in one of the vertebrae.

Some embodiments also involve using a vertebral midpoint indicator device to locate a midpoint of at least one of the two vertebrae, and marking the midpoint on one or both of the two vertebrae. An example of a midline indicator device is described by the assignees of the present application in PCT Patent Application Number 2004/000170, filed Jan. 26, 2004, the full disclosure of which is hereby incorporated by reference. Midline finding and marking are typically performed before inserting the constrained prosthesis partway into the intervertebral space. In some embodiments, locating the midpoint involves inserting the vertebral midpoint indicator device into the space between the vertebrae and imaging the midpoint indicator device using a radiographic imaging device.

In another aspect of the present invention, a method of inserting an intervertebral prosthesis into a space between two adjacent vertebrae involves sliding the prosthesis partway into the space between the vertebrae between two opposing jaws of a spacing device, removing the spacing device from the space to release the prosthesis from constraint, and pushing the unconstrained prosthesis farther into the space while allowing endplates of the prosthesis to articulate. In this method, the endplates of the prosthesis are constrained from articulating when the prosthesis is disposed between the jaws. Again, in some embodiments, the unconstrained endplates articulate about a core of the prosthesis, while in alternative embodiments they may articulate about a ball and socket joint or other structure. Such a method may optionally further include inserting the spacing device at least partway into the space and manipulating the spacing device to increase a height of the space. Any of the additional or alternative features described above may also be applied in various embodiments.

In another aspect of the present invention, a device for inserting an intervertebral prosthesis into a space between two adjacent vertebrae includes: an elongate rigid shaft having a proximal end and a distal end; an adjustable grasping member coupled with the distal end for releasably grasping endplates of the intervertebral prosthesis; and an actuator disposed near the proximal end of the shaft and coupled with the grasping member for adjusting the grasping member to grasp and release the prosthesis. The grasping member is adapted to grasp the prosthesis such that the endplates are constrained from articulating and such that the outer diameter of the grasping member does not extend beyond a largest diameter of the endplates. Additionally, the grasping member is adapted for pushing the prosthesis into the space between the two vertebrae either while grasping the prosthesis or after releasing the prosthesis.

In some embodiments, the grasping member comprises movable opposing jaws adapted to simultaneously grasp inner rims of the endplates. Such a grasping member may, for example, be coupled with the actuator via at least one rod extending through the shaft. For example, the grasping member may include a first half coupled with a first movable rod extending from the actuator and a second half coupled with a second movable rod extending from the actuator. In some embodiments, the actuator comprises a thumb screw adapted to move the first and second rods closer together and farther apart by turning the thumb screw in opposite directions. In alternative embodiments, the actuator may include, but is not limited to, a trigger, tongs and a movable handle.

In a number of embodiments, the device is shaped to pass between two opposable jaws of a vertebral spacing device disposed between the two adjacent vertebrae. Also in some embodiments, the grasping member may be adapted to push the endplates either simultaneously or individually into the space.

In another aspect of the present invention, a system for inserting an intervertebral prosthesis into a space between two adjacent vertebrae includes a prosthesis grasping device for grasping the prosthesis and pushing the prosthesis at least partway into the space and at least one prosthesis pusher device for pushing the prosthesis farther into the space. The grasping device is similar to the device described immediately above and may include any of the described features. The pusher device may include: an elongate shaft having a proximal end and a distal end; a concave pusher portion disposed at the distal end, the pusher portion adapted to push the endplates either simultaneously or individually into the space; and a handle disposed at the proximal end.

In some embodiments, the system further includes a vertebral spacing device for increasing a height of the space between the two vertebrae. An example of such a spacing device is described in PCT Patent Application Number 2004/000171, which was previously incorporated by reference. In such embodiments, the grasping member is adapted to slide through the vertebral spacing device disposed between two adjacent vertebrae. Optionally, the pusher device may also be adapted to slide through the spacing device.

The system may optionally further include a vertebral body midline indicator device for locating a midline on a vertebral body of at least one of the two vertebrae. An example of a midline indicator device is described in PCT Patent Application Number 2004/000170, which was previously incorporated by reference.

These and other aspects and embodiments will be described in further detail below, with reference to the drawing figures.

DETAILED DESCRIPTION OF THE INVENTION

Figure 1A:
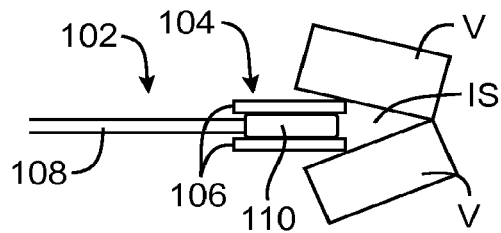
FIGS. 1A-1E demonstrate a method for inserting an intervertebral disc prosthesis according to one embodiment of the present invention.

Referring to FIGS. 1A-1E, in one embodiment a method for inserting an intervertebral disc prosthesis 104 into an intervertebral space IS between two adjacent vertebrae V first involves inserting the disc prosthesis 104 partway into the space IS while the prosthesis 104 is constrained (FIG. 1A). By "constrained" it is meant that endplates 106 of the prosthesis 104 are not free to articulate (move) about a core 112 (FIGS. 1B-1E) of the prosthesis 104. To insert the prosthesis 104 partway under constraint, an insertion device 102 may be used. Such an insertion device 102 may suitably include a grasping member 110 coupled with an elongate shaft 108. At an end opposite the grasping member 110 (not shown), the insertion device 102 may include a handle, an actuator to control the grasping member 110 and/or any other suitable features, some of which are described further below.

The prosthesis 104 may be inserted as far into the intervertebral space IS under constraint as is desired. In some embodiments, for example, the prosthesis 104 is inserted under constraint approximately one-third of the way into the space IS. In other embodiments, the prosthesis 104 may be inserted less than one-third of the way, closer to one-half of the way, or any other suitable distance into the space IS.

Figure 1B:
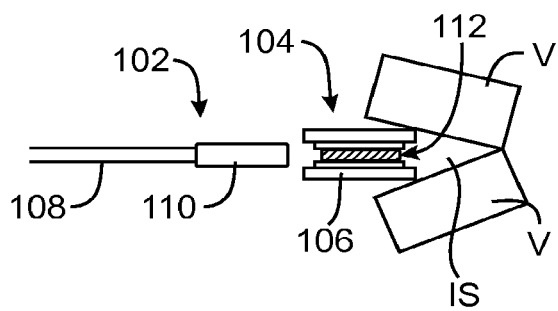

As shown in FIG. 1B, once the prosthesis 104 is inserted partway under constraint, the insertion device 102 may be removed, thus releasing the prosthesis 104 from constraint. From this point forward, the endplates 106 of the prosthesis 104 are free to move about the prosthesis core 112. Examples of such a prosthesis 104 with endplates 106 and core 112 are described by the assignees of the present application in U.S. patent application Ser. Nos. 10/855,817 and 10/855,253, previously incorporated by reference, although any other suitable prosthesis may be used in various embodiments.

Figure 1C:
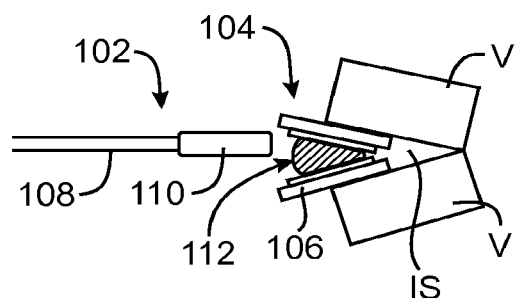
Figure 1D:
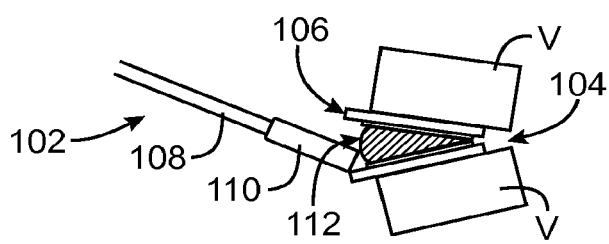
Figure 1E:
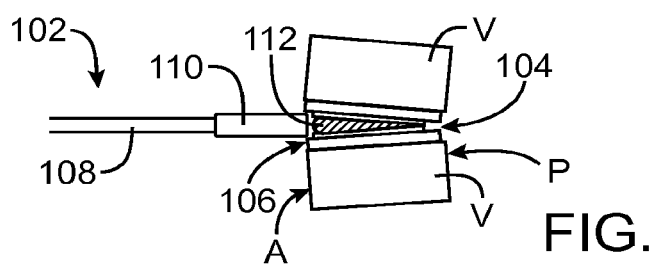

Referring now to FIGS. 1C-1E, in some embodiments the insertion device 102 may be used to push the unconstrained prosthesis 104 farther into the intervertebral space. In some embodiments, one or more separate pusher devices (not shown) may be used in addition to or instead of the insertion device 102 for pushing the prosthesis 104 farther into the space IS. FIGS. 1C and 1D demonstrate that in one embodiment the grasping member 110 of the insertion device 102 is adapted to push individually against the upper (FIG. 1C) and lower (FIG. 1D) endplates 106. As shown in FIG. 1E, the grasping member 110 may also be adapted to push simultaneously against the upper and lower endplates 106, thus pushing the prosthesis 104 as a unit farther into the intervertebral space IS.

By inserting the prosthesis 104 farther into the space IS while it is unconstrained, thus allowing the endplates 106 to articulate about the core 112, the method reduces the need for increasing the height of the intervertebral space IS by distracting the vertebrae V away from each other. Because the endplates 106 are free to articulate, the prosthesis 104 is better able to conform to the intervertebral space IS, thus reducing trauma to the vertebrae V and also limiting trauma to surrounding structures caused by over-distraction.

The unconstrained prosthesis 104 may be inserted as far into the intervertebral space IS as is desired. In some embodiments, for example, the prosthesis 104 is pushed far enough into the space IS so that a center of rotation of the prosthesis 104 is closer to a posterior edge P (FIG. 1E) of the vertebrae V than to an anterior edge A of the vertebrae V. In alternative embodiments, any other suitable insertion distance or depth may be used. Once a desired amount of insertion is achieved, the insertion device 102 is removed and the prosthesis 104 is in place between the two adjacent vertebrae V.

In various embodiments, the method just described may include fewer steps or additional steps. For example, in one embodiment, a spreader device is inserted between the two vertebrae V to spread them apart before inserting the constrained prosthesis 104. An example of such a spacing device is described in PCT Patent Application Number 2004/000171, previously incorporated by reference. In such embodiments, the insertion device 102 is typically sized to fit between opposing jaws of the spreader device. When the prosthesis 104 is partially inserted, the spreader device is removed from the intervertebral space IS, and the prosthesis 104 is released from constraint and inserted the rest of the way into the space IS. Also in some embodiments, a midline indicator device may be used to facilitate the location of a midline on one or both of the two adjacent vertebrae V. An example of such a midline indicator device is described in PCT Patent Application Number 2004/000170, previously incorporated by reference. Typically, the midline indicator is used before the disc prosthesis 104 is inserted. These and other steps or features may be included in various embodiments of the method without departing from the scope of the invention.

Figure 2A:
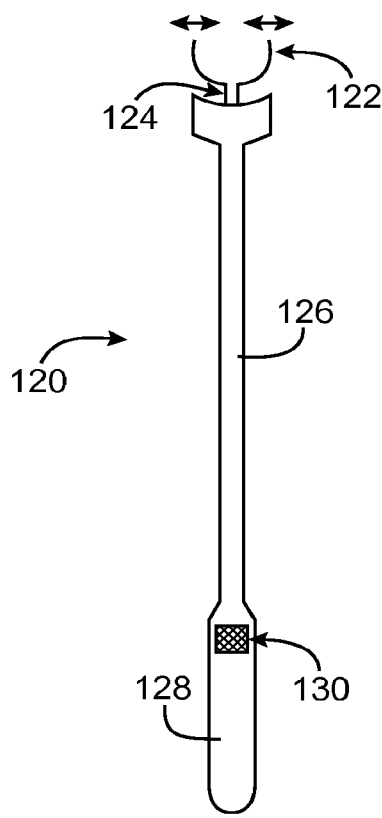
FIGS. 2A and 2B are top views of a grasping device for inserting an intervertebral disc prosthesis according to one embodiment of the present invention.
Figure 2B:
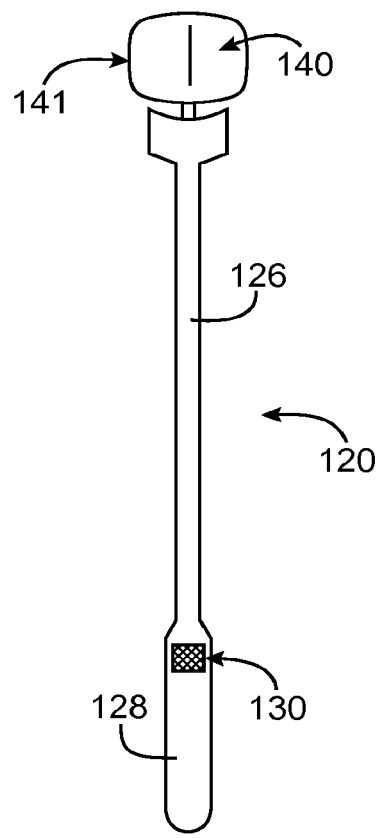
Figure 2C:
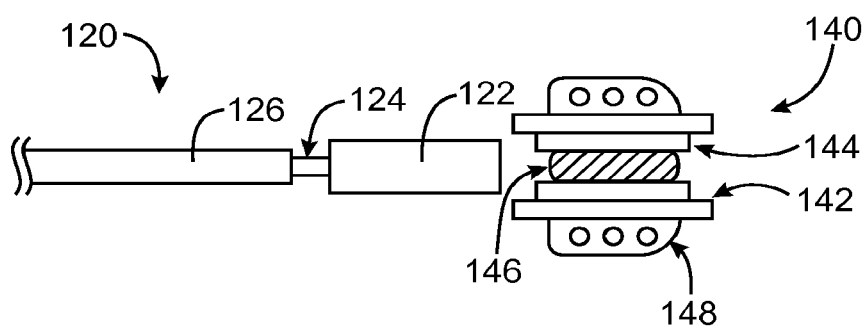
FIG. 2C is a side view of the distal end of the device in FIGS. 2A and 2B.

Referring now to FIGS. 2A-2C, one embodiment of an insertion device 120 for inserting an intervertebral disc prosthesis 140 suitably includes an elongate shaft 126, a grasping member 122 coupled with the distal end of the shaft 126, and a handle 128 at the proximal end of the shaft 120, including one or more actuators 130 for controlling movement of the grasping member 122. One or more rods 124 or other connectors extend from the grasping member 122 through the shaft 126 to the actuator 130. In the embodiment shown, for example, the grasping member 122 comprises two opposable tongs or jaws, which may be moved closer together or farther apart (double-headed arrows) via the actuator 130 and rods 124. The actuator 130 shown is a thumb screw. In alternative embodiments, scissor-type mechanisms, spring loaded tongs, a triggering mechanism or any other suitable grasping and actuating means may be used. Any suitable material or combination of materials may be used to manufacture the insertion device, including but not limited to stainless steel and/or other suitable metals.

As shown in FIG. 2B, the insertion device 120 may grasp a disc prosthesis 140 such that the grasping member 122 does not protrude beyond an outer edge 141 of the prosthesis 140. In other words, the grasping member 122 holds onto an inner portion of the prosthesis 140, so that it will not extend beyond the lateral edges 141 of the prosthesis 140. This configuration is advantageous during insertion, as the grasping member 122 is essentially out of the way, within the outer edge 141 of the prosthesis 140.

FIG. 2C is a side view of a distal end of the insertion device 120 shown in FIGS. 2A and 2B. It is more readily seen that the disc prosthesis 140 includes a core 146 and two endplates 142. Each endplate 142 includes an inner rim 144 that contacts the core 146 and a fin 148 for enhancing attachment to vertebral bone. The grasping member 122 of the insertion device 120 grasps the inner rims 144 of the endplates 142, thus positioning it within the outer edges 141 of the endplates 142. Of course, in various embodiments of the methods described herein, any suitable alternative prosthesis may be used, as well as any suitable insertion device (or devices).

Figure 3:
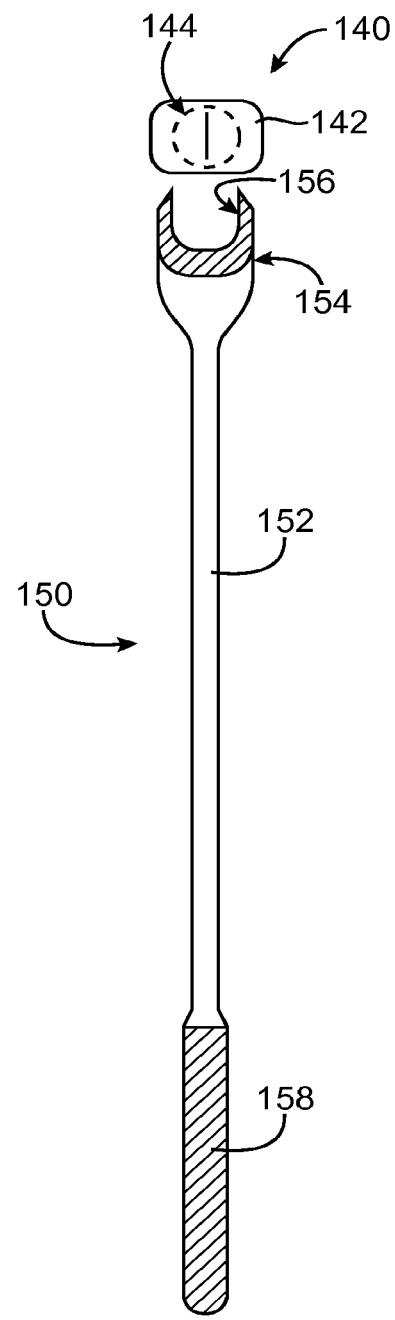
FIG. 3 is a top view of a pusher device for inserting an intervertebral disc prosthesis according to one embodiment of the present invention.

Referring now to FIG. 3, in some embodiments a separate pusher device 150 may be used to push an unconstrained prosthesis 140 farther into an intervertebral space. The pusher device 150 is typically constructed of stainless steel or other suitable metal and suitably includes an elongate shaft 152, a pusher member 154 at the distal end of the shaft 152, and a handle 158 at the proximal end of the shaft 152. The pusher member 154 includes a concave inner portion 156 for pushing against the inner rims 144 of endplates 142 of the prosthesis 140. The concave portion 156 may be tapered and/or rounded to facilitate pushing against upper and lower endplates 142 individually while also allowing for simultaneous pushing against both endplates 142. In alternative embodiments, the pusher device 150 may have any of a number of alternative configurations, shapes, sizes and the like. In some embodiments, multiple pusher devices 150 of different configurations and/or sizes are provided to allow a physician to select one or more desired devices 150.

Figure 4A:
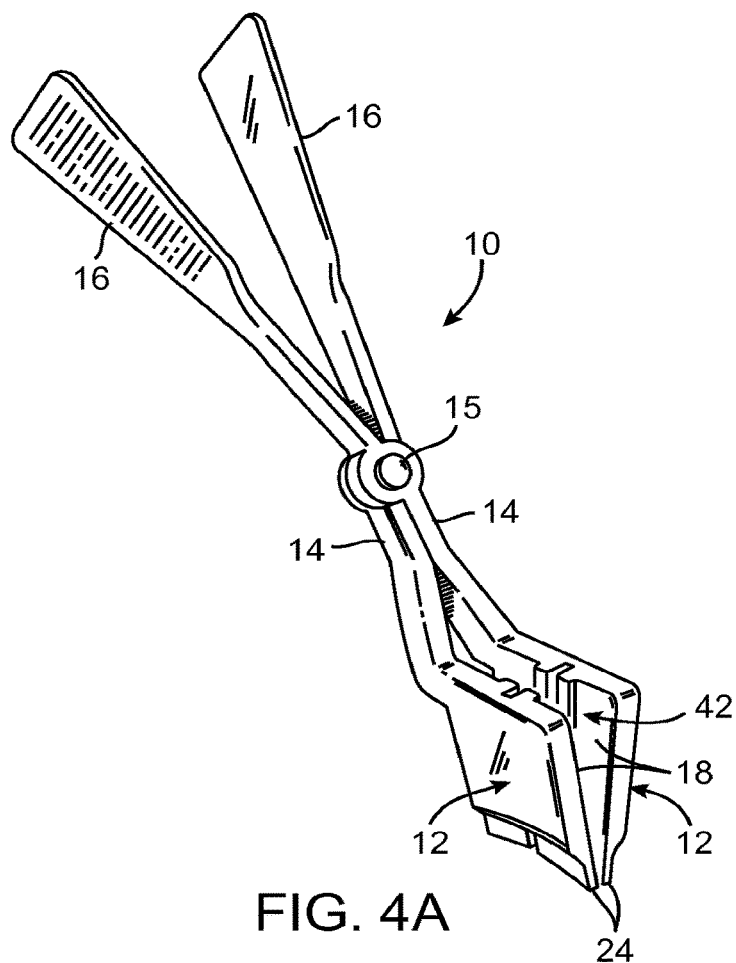
FIGS. 4A-4E are various views of a spreader device for distracting two adjacent vertebrae for inserting an intervertebral disc prosthesis according to one embodiment of the present invention.
Figure 4B:
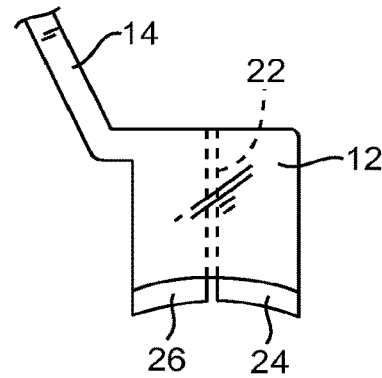

Referring now to FIGS. 4A-4E, a spreader device 10 for spreading adjacent vertebrae to facilitate intervertebral disc prosthesis 30 insertion is shown. Again, the device 10 is described in greater detail in PCT Patent Application Number 2004/000171, which was previously incorporated by reference. The spreader device 10 generally includes distally located opposable jaws 12, a slidable pusher member 45 and an actuator 15. The opposable jaws 12 are carried by arms 14 which form part of a scissors-type mechanism having a single hinge point 15. Handles 16 on the proximal end of the device are used to manipulate the opposable jaws 12. When the handles 16 are actuated, arms 14 translate the actuation motion to the single hinge point scissors type mechanism 15. This causes the opposable jaws 12 to open or close. The jaws 12 have opposing surfaces 18 formed with ribs 20 and transverse slots 22 which extend for the height of the jaws as seen in FIG. 4B. At their free ends, the jaws 12 are provided with relatively sharp tips or blades 24 having curved extremities 26.

FIGS. 4A and 4B illustrate how the handles 14 are inclined relative to the jaws 12. Manipulation of the handles 16 by moving them causes the jaws 12 to open or close. Other embodiments include a double hinge instead of the single hinge 15 which would pivot the jaws apart from one another when the handles 16 are displaced towards one another.

The insertion device 10 illustrated in FIGS. 4A-4E is designed for placement of an intervertebral prosthetic disc 30. Such a prosthetic disc 30 comprises opposing endplates 32 which are located on opposite sides of a central core 34. The opposing endplates 32 articulate about the central core 34. The prosthetic disc 30 also comprises projecting fins 36 which are aligned with matching slots 40 in the vertebrae 38 during implantation. Typically slots 40 are saw cut into the vertebrae 38.

Figure 4C:
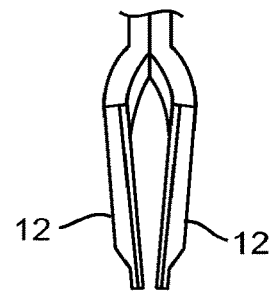
Figure 4E:
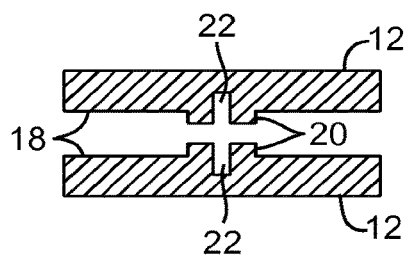
Figure 4D:
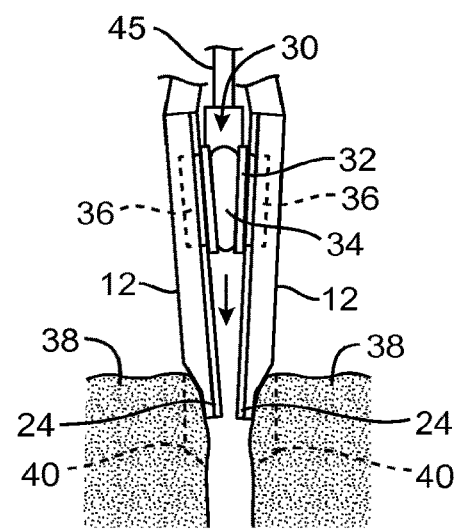
Figure 5:
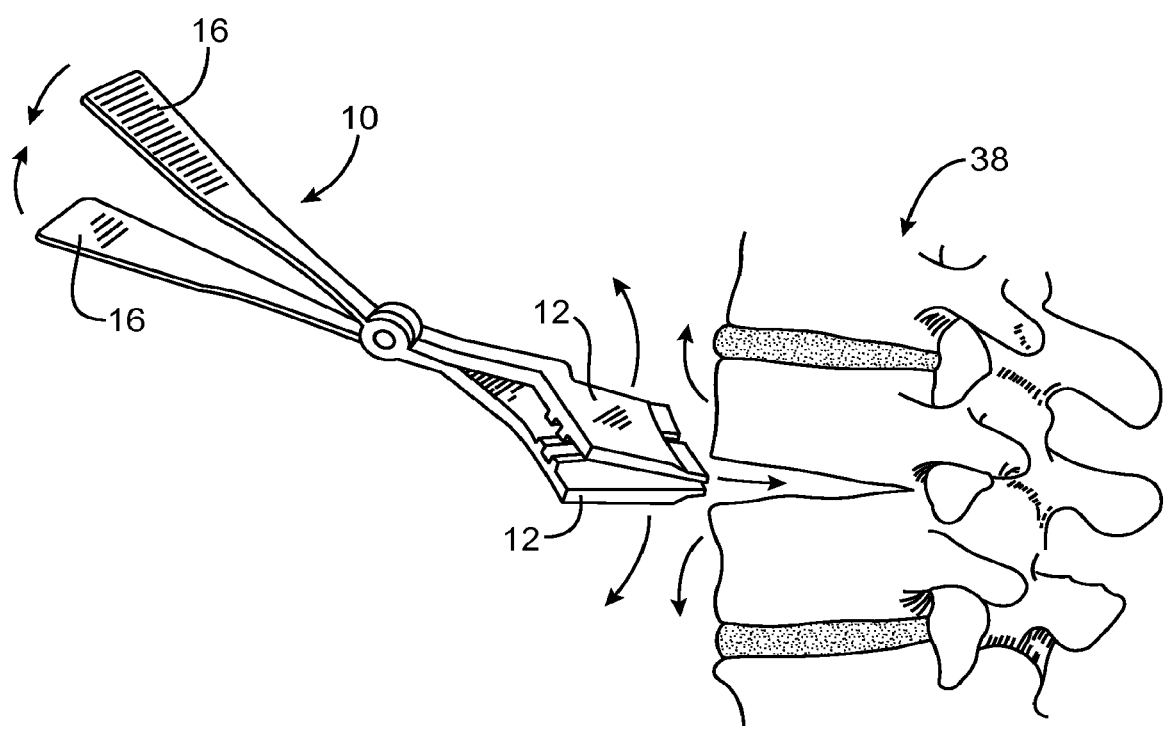
FIG. 5 demonstrates the spreading action of the spreader device in FIGS. 4A-4E.
Figure 6A:
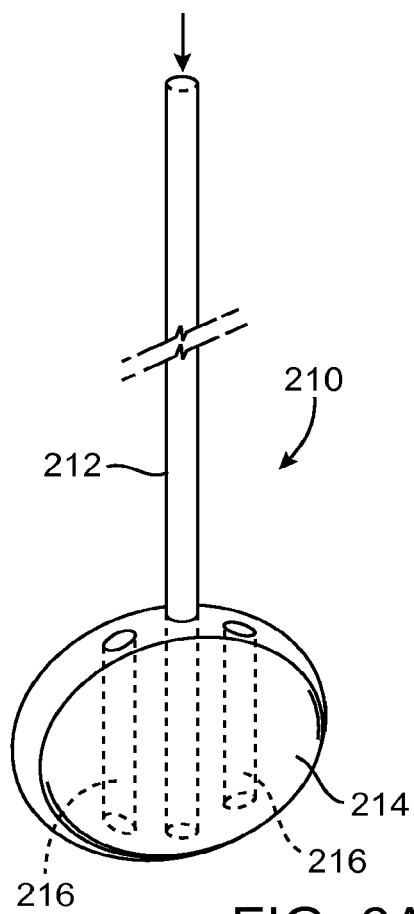
FIGS. 6A-6D are various views of a vertebral body midline indicator device according to one embodiment of the present invention.
Figure 6B:
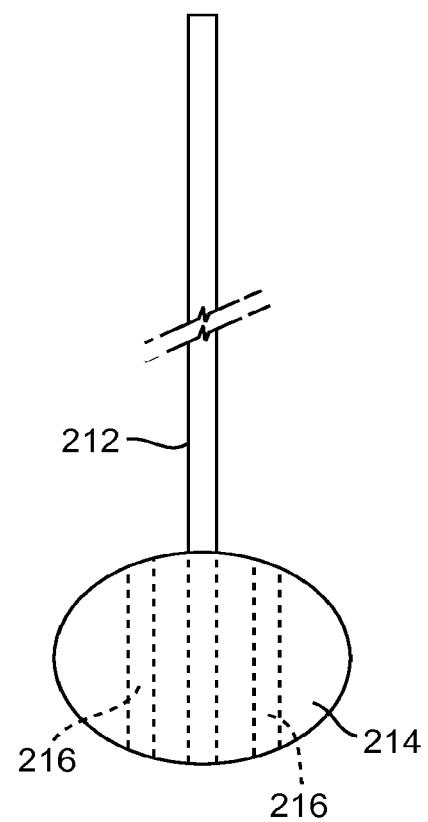
Figure 6C:
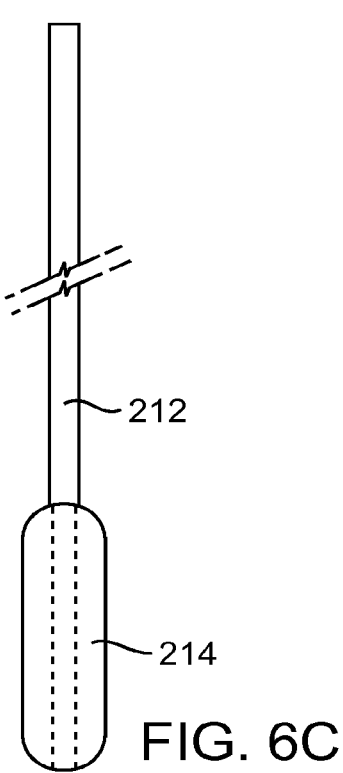
Figure 6D:
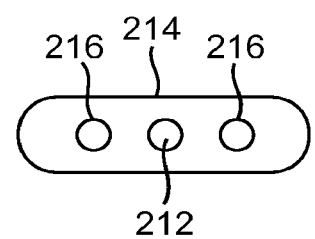

A method of inserting the intervertebral prosthesis is illustrated in FIGS. 4D and 5. In order to place the prosthesis 30, the vertebrae 38 are distracted by a distance sufficient for at least partial insertion of the prosthesis 30. To achieve this, the tips 24 of the opposable jaws 12 are inserted between the vertebrae 38 with the slots 22 in the opposable jaws 12 aligned with the slots in the vertebrae 40. The handles 16 are then manipulated to force the opposable jaws 12 apart which also forces the vertebrae 38 apart from one another, creating a gap. The prosthesis 30 is then inserted into the gap 42 between the opposable jaws 12 where it is held therein with fins 36 engaged with the corresponding slots 22. The prosthesis 30 is then slipped distally in the gap while being guided by the fins 36 cooperating with the slots 22. The prosthesis 30 is moved through the inter jaw gap and past the jaw tips 24 in order to locate the prosthesis 30 between the vertebrae 38 with fins 36 in the vertebral cut slots 40. The slots 22 in the opposable jaws 12 help to guide the fins 36 into the vertebral cut slots 40.

FIG. 4C illustrates the jaws 12 inclined towards one another, in the direction towards the tips 24. The gap 42 between the jaws 12 at the top is large enough for insertion of the prosthesis 30 between them at that point. Therefore, in an alternative method of placing the prosthesis, the prosthesis 30 may be located initially in the gap 42 and then it may be pushed down towards the tip 24, forcing the jaws 12 open and similarly forcing the vertebrae 38 apart from one another. A pusher 45 may be used to hold, position and drive the prosthesis 30 during the placement procedure. A force may be applied manually to pusher 45 or it may be tapped on the upper end to drive the prosthesis downward.

Alternatively, the prosthesis placement procedure may be modified so that the initial distraction of the vertebra 38 is achieved by manipulation of the handles 16 and then a force may be applied manually to the pusher 45 or it may be tapped in order to create the final intervertebral gap and placement of the prosthesis 30. The spreader device 10 serves both to facilitate insertion of the prosthesis 30 between the vertebrae 38 and also to ensure that the prosthesis 30 is accurately guided into position with its fins 36 lined up with the vertebral slots 40.

FIG. 5 shows in greater detail (solid-tipped arrows) the various motions involved in inserting the spreader device 10 into the intervertebral space and manipulating the handles 16 to force open the jaws 12 and thus increased the height of the intervertebral space between the two adjacent vertebrae 38. As mentioned above, use of this or other spreader devices 10 is optional and is not required in all embodiments.

FIGS. 6A-6D show another optional device for use in the insertion methods of the present invention. As mentioned above, a midline indicator device 210 such as the one shown is described in greater detail in PCT Patent Application Number 2004/000170, which was previously incorporated by reference. The midline indicator 210 suitably includes an elongate shaft 212 and a body 214 coupled with one end of the shaft 212. The shaft 212 may be made of one or more radiopaque materials, such as but not limited to stainless steel, titanium or the like. Alternatively, the shaft 212 may be radiolucent. The body 214 is made of one or more radiolucent materials, such as a polymer, so that it is not visible on radiographs. Embedded in the body 214 are two elongate radiopaque markers 216, also made of any suitable radiopaque material(s). The markers 216 are parallel to the shaft 212 and are located on opposite sides and equidistant from the shaft 212.

Figure 7A:
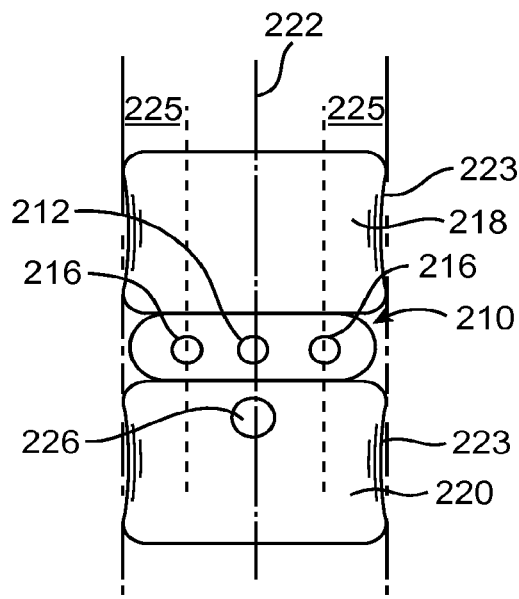
FIGS. 7A and 7B demonstrate indication of vertebral midline using the device in FIGS. 6A-6D.
Figure 7B:
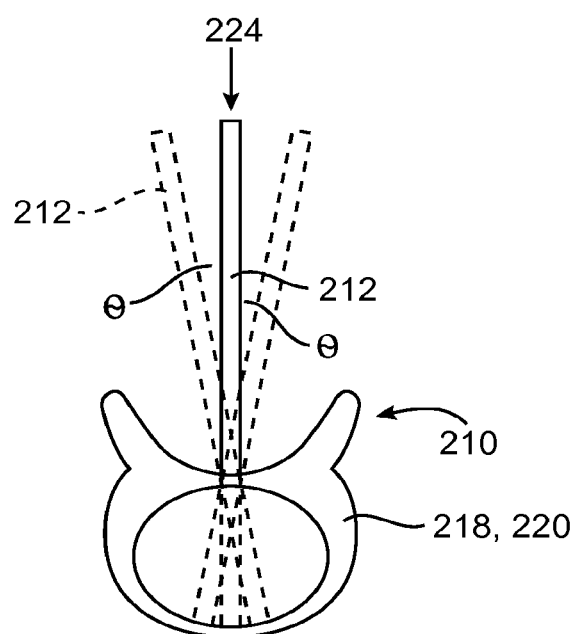

FIGS. 7A and 7B demonstrate a method for using the midline indicator to find a vertebral body midline 222. FIG. 7A shows, in anterior view, adjacent upper 218 and lower 220 vertebrae. To determine the midline 222, the surgeon uses the shaft 212 to insert the body 214 between the vertebrae 218, 220. The surgeon then attempts to position the shaft 212 at the vertebral midline 222, and a radiograph is taken of the vertebrae 218, 220 and indicator 210 from the anterior-posterior (A-P) direction. The surgeon then examines the radiograph to determine whether the markers 216 are equidistant laterally from the lateral osseous edges 223 of the vertebrae 218, 220—i.e., that the distance 225 is the same on both sides, and that the markers 216 are aligned with the pedicles.

Additionally, if the shaft 212 and markers 216 are properly aligned in the A-P direction, they will appear as dots on the radiograph. If the midline indicator 210 is turned, however, as is demonstrated by the dotted lines in FIG. 7B, the shaft 212 and markers 216 will show up as lines or stretched-out dots on the radiograph. The A-P direction of the radiograph is shown by 224, with misalignment of the indicator 210 shown by angles θ. By consulting one or more radiographs and manipulating the indicator 210, the surgeon positions the handle 212 of the indicator 210 at the vertebral midline 222. The surgeon may then make a mark 226 in one or more vertebrae 218, 220 to indicate the midline 222. The mark 226 may be made by any suitable means, such as by burning with an electrocautery device, marking with a marking pen, inserting a pin, or the like. After one or more midline marks 226 are made, the midline indicator 210 is removed and the disc prosthesis (not shown) is inserted. Again, the midline finding step is optional.

Although the foregoing is a complete and accurate description of the invention, any suitable modifications, additions or the like may be made to the various embodiments without departing from the scope of the invention. Therefore, nothing described above should be interpreted as limiting the scope of the invention as it is described in the following claims.

What is claimed is:

1. A system for inserting an intervertebral prosthesis into a space between two adjacent vertebrae, the system comprising:
   an intervertebral prosthesis having two endplates movable with respect to one another, wherein the two endplates of the intervertebral prosthesis have a width in a lateral direction of the endplates between opposite lateral sides of the endplates, wherein the width is greater than a depth in an anterior/posterior direction of the endplates;
   a prosthesis grasping device, wherein the prosthesis grasping device is configured to insert the two endplates in an assembled configuration into the space between two adjacent vertebrae and wherein the prosthesis grasping device is configured to grasp the two endplates from an anterior side of the endplates with movable opposing jaws configured to articulate laterally in a same plane as the width of the intervertebral prosthesis; and
   at least one prosthesis pusher device which is discrete from the prosthesis grasping device, the prosthesis pusher device having a distal end configured to push against the endplates of the intervertebral prosthesis, wherein after the intervertebral prosthesis is inserted into the space, the at least one prosthesis pusher device is used to engage and push the prosthesis farther into the space.

2. A system as in claim 1, wherein the prosthesis grasping device is shaped to pass between two opposable jaws of a vertebral spacing device disposed between the two adjacent vertebrae.

3. A system as in claim 1, wherein the at least one pusher device comprises:
   an elongate shaft having a proximal end and a distal end;
   a concave pusher portion disposed at the distal end, the pusher portion adapted to push the endplates either simultaneously or individually into the space; and
   a handle disposed at the proximal end.

4. A system as in claim 1, wherein the distal end of the at least one pusher device has a concave shape configured for pushing against inner rims of the two endplates.

5. A system as in claim 1, wherein the intervertebral prosthesis includes a core and the grasping member is configured to grasp the two endplates of the intervertebral prosthesis with the core located between the endplates.

6. A system as in claim 5, wherein inner rims of the intervertebral prosthesis surround the core when the core is located between the endplates.

7. A system as in claim 1, wherein the two endplates of the intervertebral prosthesis are separable from each other.

8. A system for inserting an intervertebral prosthesis into a space between two adjacent vertebrae, the system comprising:
   an intervertebral prosthesis having two endplates movable with respect to one another, wherein the two endplates of the intervertebral prosthesis have a width in a lateral direction of the endplates between opposite lateral sides of the endplates, wherein the width is greater than a depth in an anterior/posterior direction of the endplates;
   a prosthesis grasping device, wherein the prosthesis grasping device is configured to insert the two endplates in an assembled configuration into the space between two adjacent vertebrae and wherein the prosthesis grasping device is configured to grasp the two endplates from an anterior side of the endplates with movable opposing jaws configured to articulate laterally in a same plane as the width of the intervertebral prosthesis, and shaped to simultaneously grasp an inner rim of each of the two endplates; and
   at least one prosthesis pusher device which is discrete from the prosthesis grasping device, the prosthesis pusher device having a distal end configured to push against the endplates of the intervertebral prosthesis, wherein after the intervertebral prosthesis is inserted into the space, the at least one prosthesis pusher device is used to engage and push the prosthesis farther into the space.

9. A system as in claim 8, wherein the prosthesis grasping device is shaped to pass between two opposable jaws of a vertebral spacing device disposed between the two adjacent vertebrae.

10. A system as in claim 8, wherein the at least one pusher device comprises:
    an elongate shaft having a proximal end and a distal end;
    a concave pusher portion disposed at the distal end, the pusher portion adapted to push the endplates either simultaneously or individually into the space; and
    a handle disposed at the proximal end.

11. A system as in claim 8, wherein the distal end of the at least one pusher device has a concave shape configured for pushing against the inner rims of each of the two endplates.

12. A system as in claim 8, wherein the intervertebral prosthesis includes a core and the grasping member is configured to grasp the two endplates of the intervertebral prosthesis with the core located between the endplates.

13. A system as in claim 8, wherein the two endplates of the intervertebral prosthesis are separable from each other.

14. A system as in claim 13, wherein the inner rims of each of the two endplates of the intervertebral prosthesis collectively surround the core when the core is located between the endplates.

15. A system for inserting an intervertebral prosthesis into a space between two adjacent vertebrae, the system comprising:
an intervertebral prosthesis having two endplates movable with respect to one another, wherein the two endplates of the intervertebral prosthesis have a width in a lateral direction of the endplates between opposite lateral sides of the endplates, wherein the width is greater than a depth in an anterior/posterior direction of the endplates;
a prosthesis grasping device, wherein the prosthesis grasping device is configured to insert the two endplates in an assembled configuration into the space between two adjacent vertebrae, the prosthesis grasping device includes an actuator for actuating a pair of laterally moveable opposing jaws shaped to grasp the two endplates from an anterior side of the endplates, and wherein the movable opposing jaws articulate laterally in a same plane as the width of the intervertebral prosthesis, and are shaped to simultaneously grasp an inner rim of each of the two endplates; and
at least one prosthesis pusher device which is discrete from the prosthesis grasping device, the prosthesis pusher device having a distal end configured to push against the endplates of the intervertebral prosthesis, wherein after the intervertebral prosthesis is inserted into the space, the at least one prosthesis pusher device is used to engage and push the prosthesis farther into the space.

16. A system as in claim 15, wherein the opposing jaws of the prosthesis grasping device are shaped to pass between two opposable jaws of a vertebral spacing device disposed between the two adjacent vertebrae.

17. A system as in claim 15, wherein the at least one pusher device comprises:
an elongate shaft having a proximal end and a distal end;
a concave pusher portion disposed at the distal end, the pusher portion adapted to push the endplates either simultaneously or individually into the space; and
a handle disposed at the proximal end.

18. A system as in claim 17, wherein the distal end of the at least one pusher device has a concave shape configured for pushing against the inner rims of the two endplates.

19. A system as in claim 15, wherein the two endplates of the intervertebral prosthesis are separable from each other.

20. A system as in claim 15, wherein the intervertebral prosthesis includes a core and the two opposable jaws of the grasping member are configured to grasp the two endplates of the intervertebral prosthesis with the core located between the endplates.

* * * * *